United States Patent [19]

Campbell

[11] Patent Number: 4,593,028

[45] Date of Patent: * Jun. 3, 1986

[54] 5-HETERO ARYL-SUBSTITUTED-2-PYRIDONES USEFUL AS CARDIOTONIC AGENTS FOR TREATMENT OF CONGESTIVE HEART FAILURE

[75] Inventor: Henry F. Campbell, Lansdale, Pa.

[73] Assignee: William H. Rorer, Inc., Fort Washington, Pa.

[*] Notice: The portion of the term of this patent subsequent to Feb. 21, 2001 has been disclaimed.

[21] Appl. No.: 619,388

[22] PCT Filed: Mar. 4, 1983

[86] PCT No.: PCT/US83/00291

§ 371 Date: Apr. 19, 1984

§ 102(e) Date: Apr. 19, 1984

Related U.S. Application Data

[63] Continuation-in-part of Ser. No. 314,692, Oct. 26, 1981, Pat. No. 4,514,400.

[51] Int. Cl.$^4$ .............. A61K 31/505; A61K 31/495; C07D 239/02; C07D 401/00

[52] U.S. Cl. .................................. 514/256; 514/252; 514/341; 544/238; 544/239; 544/240; 544/241; 544/317; 544/320; 544/333

[58] Field of Search ...................... 544/333, 405, 238; 424/250, 251

[56] References Cited

U.S. PATENT DOCUMENTS 4,107,315 8/1978 Lesher ................................ 424/263
4,432,979 2/1984 Campbell ........................... 424/251

FOREIGN PATENT DOCUMENTS 2070606 9/1981 United Kingdom .

*Primary Examiner*—Donald G. Daus
*Assistant Examiner*—Cecilia Shen
*Attorney, Agent, or Firm*—James A. Nicholson; Alexis Barron; Martin F. Savitzky

[57] ABSTRACT

Cardiotonic 5-heteroaryl-substituted-2-pyridone compounds, pharmaceutical compositions, and a method for the treatment of congestive heart failure.

1 Claim, No Drawings

5-HETERO ARYL-SUBSTITUTED-2-PYRIDONES USEFUL AS CARDIOTONIC AGENTS FOR TREATMENT OF CONGESTIVE HEART FAILURE

This application is a continuation-in-part application of copending Ser. No. 314,692, filed Oct. 26, 1981, U.S. Pat. No. 4,514,400.

FIELD OF THE INVENTION

This invention relates to novel 5-heteroaryl-substituted-2-pyridones, useful as cardiotonic agents for the treatment of congestive heart failure, to their preparation and to pharmaceutical compositions comprised thereof.

REPORTED DEVELOPMENTS

Congestive heart failure is a life-threatening condition in which myocardial contractility is depressed so that the heart is unable to adequately pump the blood returning to it. Normal pathologic sequelae include decreased cardiac output, venous pooling, increased venous pressure, edema, increased heart size, increased myocardial wall tension, and eventually cessation of contractility. Digitalis glycosides have long been used to increase myocardial contractility and reverse the detrimental changes seen in congestive heart failure. More recently, dopamine, dobutamine, and amrinone have been used to provide necessary inotropic support for the failing heart.

Other reported inotropic drugs include the 5-pyridyl substituted pyridones, reported by Lesher and Opalka, where cardiotonic activity is exhibited when the substituents in the 3-position of the pyridones are hydrogen, cyano, amino, acetylamino, loweralkylamino, or diloweralkylamino (see U.S. Pat. Nos. 4,004,012, 4,072,746, 4,107,315, 4,137,233); when the 3-position of the pyridone is substituted by diloweralkyl amino methylene malonate (see U.S. Pat. No. 4,199,586); and when the 3-position is acylamino (see U.S. Pat. No. 4,271,168). The most preferred 5-pyridyl-pyridone, "Amrinone", 3-amino-5-(4-pyridyl)-2(1H)-pyridone, is reported to cause a 39 to 98% increase in cardiac contractile force with a duration of action of more than three hours at doses of 1.9 to 10 mg/kg, as reported in U.S. Pat. No. 4,107,315. At 10 mg/kg, however, an increase in heart rate is observed.

Bormann has reported other 3-amino substituted pyridone cardiotonics having various heterocyclic substituents in the 5-position (GB 2070606A; PCT published Appl. No. PCT/CH81/00023).

Lesher and Opalka have reported that 5-(4-pyridyl)-pyridones where the 3-position is halo substituted are useful intermediates for the preparation of compounds having cardiotonic properties. Pyridones wherein the 5-position is substituted by a heteroaryl group other than pyridyl and the 3-position is other than amino have not been reported to have positive inotropic activity or cardiotonic activity.

The present invention relates to a class of novel 5-heteroaryl-3-substituted pyridones which exhibit cardiotonic activity in humans and mammals and which have the advantage of producing relatively small increases in heart rate at doses producing a positive inotropic effect.

SUMMARY OF THE INVENTION

This invention relates to the novel compounds described by the structural Formula I:

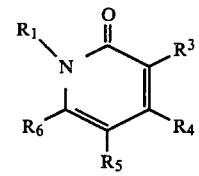

wherein:
- $R_1$ is hydrogen, alkyl, hydroxyalkyl, or phenloweralkyl;
- $R_3$ is hydrogen, halo or haloalkyl;
- $R_4$ and $R_6$ are each independently hydrogen or alkyl;
- $R_5$ is a 6 membered ring heteroaryl ring including two nitrogen atoms in the ring, wherein one or more of the hetero ring hydrogen atoms may be substituted by halo, alkyl, haloalkyl, hydroxyalkyl, hydroxy, alkylamino, dialkylamino, amino, acylamino, cyano or nitro; and, salts thereof.

This invention also relates to methods of preparing the compounds of Formula I, to pharmaceutical compositions for use in increasing cardiac contractility in humans and to the uses of these compunds in the treatment of cardiac failure in humans and other mammals.

DETAILED DESCRIPTION

Certain of the compounds of Formula I may exist in enolic or tautomeric forms, and all of these forms are considered to be included within the scope of this invention.

The compounds of this invention which have particular usefulness as cardiotonic agents are described by the Formulae II to VII.

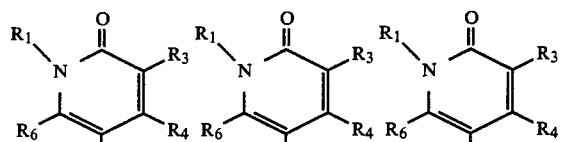

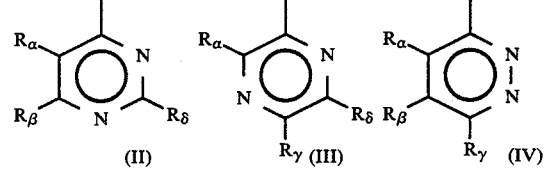

wherein:
$R_1$, $R_3$, $R_4$ and $R_6$ are as described above, and $R_\alpha$, $R_\beta$, $R_\gamma$, $R_\delta$ and $R_\epsilon$ are each independently hydrogen, halo, alkyl, haloalkyl, hydroxyalkyl, hydroxy, dialkylamino, alkylamino, amino, acylamino, cyano or nitro.

The more preferred compounds are those disclosed by Formulae II to VII, wherein:

$R_1$ is hydrogen, loweralkyl of $C_1$–$C_3$ carbon atoms or hydroxyloweralkyl of $C_2$–$C_3$ carbon atoms;

$R_3$ is hydrogen, halo or haloloweralkyl of $C_1$–$C_3$ carbon atoms;

$R_4$ is hydrogen or loweralkyl of $C_1$–$C_3$ carbon atoms;

$R_6$ is hydrogen or loweralkyl of $C_1$–$C_3$ carbon atoms;

$R_\alpha$, $R_\beta$, $R_\gamma$, $R_\delta$ and $R_{6\delta}$ are hydrogen or loweralkyl.

Most preferred are those compounds disclosed by Formulae II to VII, wherein:

$R_1$ is methyl, ethyl or hydroxyethyl;

$R_3$ is hydrogen, fluoro, chloro, bromo or trifluoromethyl;

$R_4$ is hydrogen;

$R_6$ is hydrogen, methyl or ethyl and $R_\alpha$, $R_\beta$, $R_\gamma$, $R_\delta$ and $R_\epsilon$ are hydrogen, methyl or ethyl.

A special embodiment of the preferred compounds includes those compounds of Formula I, wherein:

$R_1$ is methyl, ethyl or hydroxyethyl;

$R_3$ is fluoro, chloro, bromo or trifluoromethyl;

$R_4$ is hydrogen;

$R_5$ is 4-pyrimidinyl, 2-pyrazinyl, 3-pyridazinyl, 2-pyrimidinyl or 4-pyridazinyl; and $R_6$ is methyl or ethyl.

Other embodiments include those compounds wherein:

$R_1$, $R_3$ and $R_4$ are all hydrogen;

$R_1$, $R_4$ and $R_6$ are all hydrogen;

$R_3$, $R_4$ and $R_6$ are all hydrogen;

$R_1$ and $R_4$ are both hydrogen;

$R_3$ and $R_4$ are both hydrogen;

$R_4$ and $R_6$ are both lower alkyl;

$R_4$ and $R_6$ are both hydrogen; or at least one of $R_\alpha$, $R_\beta$, $R_\gamma$, $R_\delta$ and $R_\epsilon$ is other than hydrogen.

As employed above and throughout the disclosure, the following terms, unless otherwise indicated, shall be understood to have the following meanings:

"Alkyl" means a saturated aliphatic hydrocarbon which may be either straight- or branched-chained containing from about one to about 5 carbon atoms.

"Lower alkyl" means an alkyl group as above, having 1 to about 3 carbon atoms.

The term "halo" includes all four halogens; namely, fluorine, chlorine, bromine and iodine.

"Haloalkyl" refers to a loweralkyl hydrocarbon group which may be substituted by one or more halo groups, such trifluoromethyl, trifluorethyl, chloromethyl, etc.

"Phenloweralkyl" means a lower alkyl group in which one or more hydrogens is substituted by a phenyl group. Preferred groups are benzyl and phenethyl, etc.

"Acylamino" means an amino group substituted by an acyl radical of a lower alkanoic acid such as acetyl, propionyl, butyryl, valeryl or stearoyl.

"Hydroxy alkyl" means an alkyl group substituted by a hydroxy group. Preferred hydroxy loweralkyl groups include hydroxymethyl, 2-hydroxyethyl, 2-hydroxypropyl, or 3-hydroxypropyl.

The compounds of this invention may be useful both in the free base form and in the form of salts, and both forms are within the scope of the invention. Acid addition salts can be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. In practicing the invention it is convenient to form the free base form; however, appropriate pharmaceutically acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

When a base is used for salt formation, it is preferred to form the same from a sodium or potassium base such as sodium hydroxide or potassium hydroxide.

Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures.

The compounds of this invention may be prepared by one of the following synthetic routes.

The pyridone ring may be formed in essentially two steps by first reacting a heteroarylmethyl compound with an appropriate activated methylidene reagent such as a Vilsmeier reagent and thereby result in the formation of the iminium salt of the α-heteroaryl, β-enamino ketone or aldehyde. If desired, the iminium salt may be hydrolyzed to the β-enamino ketone or aldehyde for use in subsequent steps. An exemplary reaction is detailed in Scheme I.

Scheme I

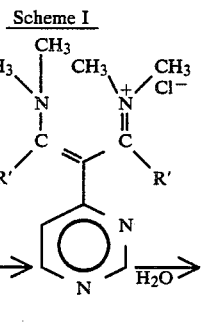

-continued
Scheme I

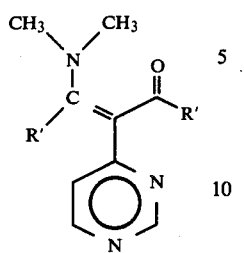

The substitution pattern in the final product is predetermined in this reaction sequence by the choice of activated methylidene reagent which ensures symmetry in the $R_4$ and $R_6$ position of the final product. The activated methylidene reagent provides the carbon units which, in this reaction sequence, form the $C-R_4$ and $C-R_6$ groups of the pyridone ring. By choosing dimethylacetamide (R'=Me), for example, both $R_4$ and $R_6$ are methyl in the final product. Treatment of the α,β-enamino carbonyl compound or the iminum salt thereof with α-cyano acetamide in the presence of base results in the 3-cyano pyridone VIII, which may be hydrolyzed to the 3-carbamoyl compound IX or the 3-carboxylic acid X. (Scheme II)

-continued
Scheme II

IX          X

Assymetry in the $R_4$ and $R_6$ positions of the final product may be introduced by using a heteroarylketone as the starting material. The treatment of the α,β-enamino ketone with an appropriate nucleophile, such as α-cyanoacetamide in the presence of base, provides that R' will occupy the $R_4$ position of the pyridone. (Scheme III)

Scheme III

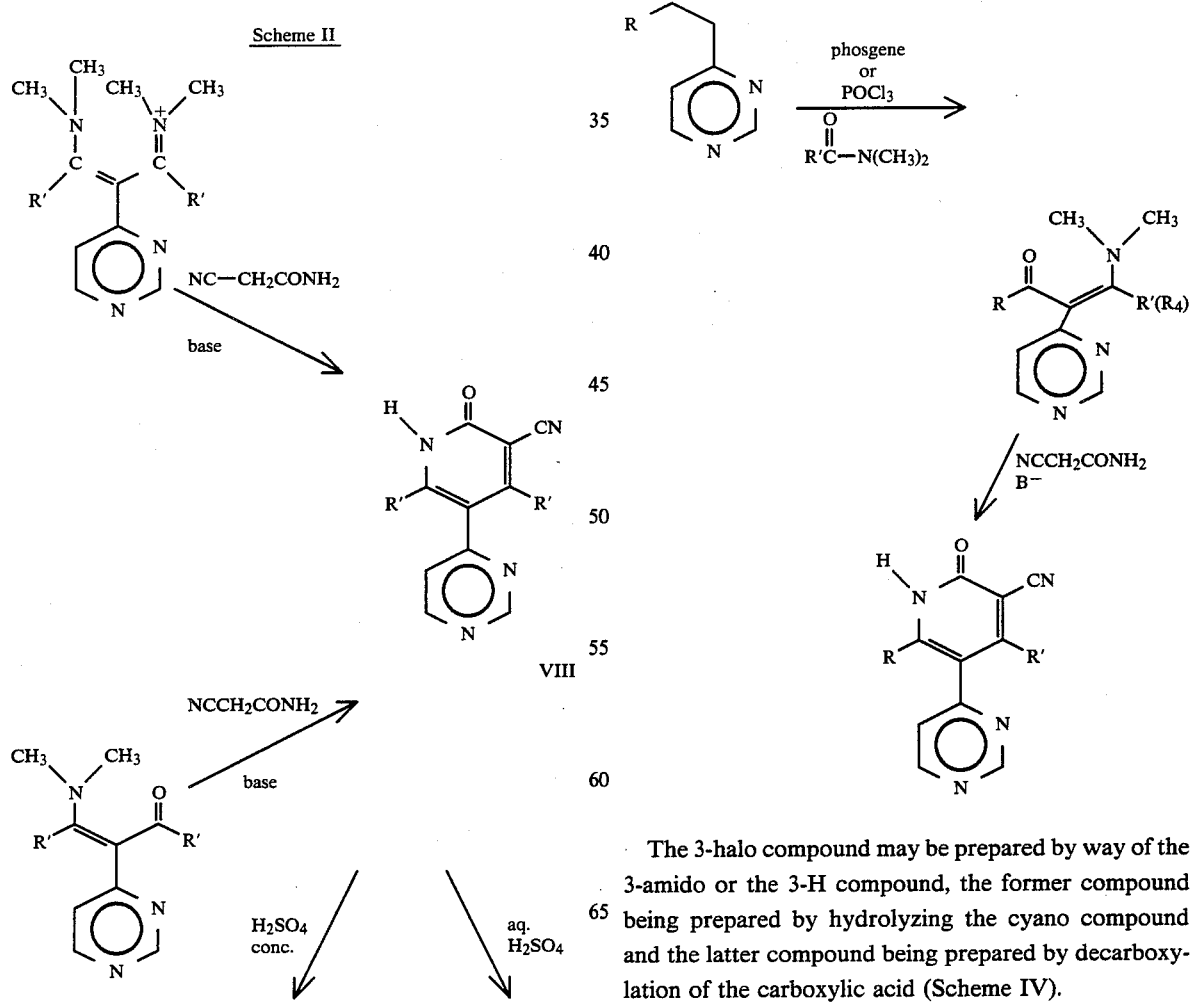

The 3-halo compound may be prepared by way of the 3-amido or the 3-H compound, the former compound being prepared by hydrolyzing the cyano compound and the latter compound being prepared by decarboxylation of the carboxylic acid (Scheme IV).

Scheme IV

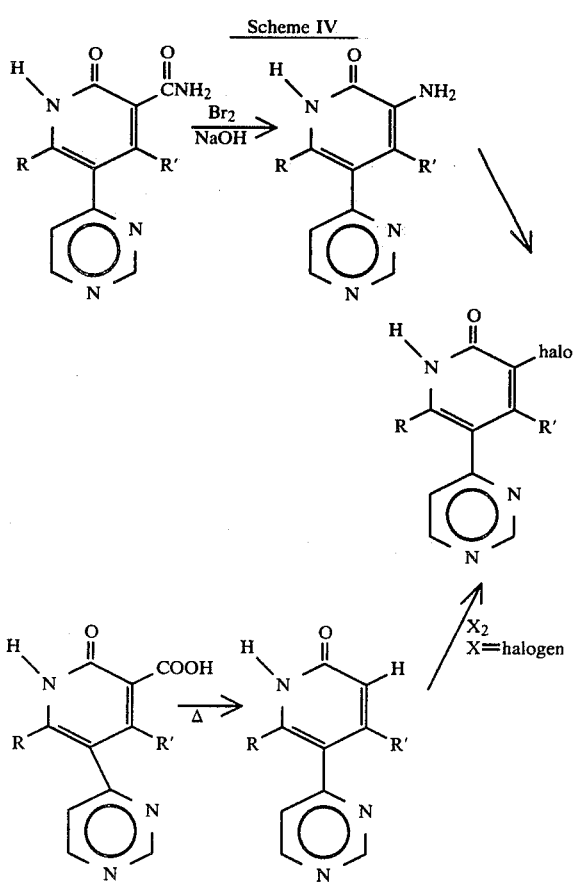

The 3-trifuoromethyl compound XI may be prepared by treating the 3-carboxy compound X with diethylamino sulfur trifluoride (Scheme V).

Scheme V

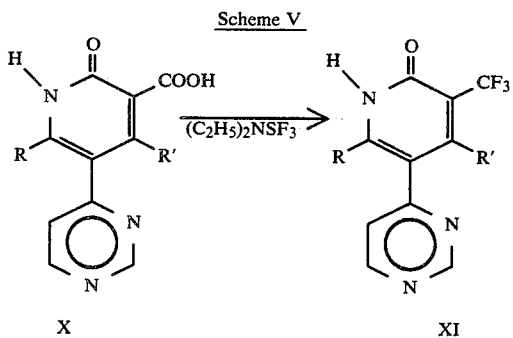

The following are illustrative examples of the preparation of the compounds of this invention and should not be construed as limitations thereof.

EXAMPLE I

THE PREPARATION OF 3-BROMO-5-(4-PYRIMIDINYL)-2(1H)-PYRIDONE

Step 1. α-(4-Pyrimidinyl)-β-dimethylaminoacrolein

A chilled solution of 324 g of phosgene in 1 liter of chloroform is added to a mixture of 700 ml of chloroform and 620 ml of DMF cooled to −5° C. The mixture is stirred for 15 minutes and a solution of 98.1 g of methyl pyrimidine in 50 ml of chloroform is added dropwise over a period of 25 minutes at a temperature of 0° C. The reaction mixture is stirred at 0° C. for 15 minutes and allowed to warm to RT. The reaction mixture is refluxed for one hour, cooled in an ice bath, and filtered. The filtered solid is washed with chloroform and dried in vacuo at 70° C. yielding the desired imino salt as a light yellow solid. The solid is dissolved in distilled $H_2O$ and chilled in an ice bath. Anhydrous potassium carbonate is added slowly to the aqueous solution until neutral and additional potassium carbonate (5 g) and chloroform are added. The basic solution is stirred overnight. The reaction mixture is extracted with chloroform, the chloroform extract is dried over sodium sulfate and the chloroform removed in vacuo. The residue crystallizes to yield α-(4-pyrimidinyl)-β-dimethylaminoacrolein.

Step 2. 3-Cyano-5-(4-pyrimidinyl)-2(1H)-pyridone 27 g of sodium methoxide in 200 ml of methanol are added to a solution of 49.8 g of α-(4-pyrimidinyl)-β-dimethylaminoacrolein and 33.6 g of 2-cyanoacetamide in 450 l of methanol under a nitrogen atmosphere. The reaction mixture is heated to reflux for 5 minutes, cooled and filtered. The resulting solid is washed with cold methanol, ether, partially air dried, dissolved in 2 l of distilled $H_2O$ and filtered to remove a small amount of undissolved impurity. The filtrate is acidified to a pH of 6 by addition of 6N HCl. The resultant precipitate is filtered, washed with $H_2O$ and dried, yielding the desired 3-cyano-5-(4-pyrimidinyl)-2(1H)-pyridone as a solid, M.P.>250° C.

Step 3. 1,2-Dihydro-2-oxo-5-(4-pyrimidinyl)-nicotinic acid

A solution of 23.0 g of 3-cyano-5-(4-pyrimidinyl)-2(1H)-pyridone in 300 ml of 50% aqueous $H_2SO_4$ is heated to reflux for 5 hours and allowed to cool to RT. The reaction mixture is poured onto about 1 kg of crushed ice with stirring. The resulting precipitate is filtered, washed with distilled $H_2O$, isopropanol and ether and dried in vacuo overnight. The dried solid is added to $H_2O$ and neutralized with NaOH. The resultant solid is filtered, washed with $H_2O$, methanol and ether and recrystallized from DMF, yielding the nicotinic acid as a white solid, M.P.>250° C.

Step 4. 5-(4-Pyrimidyl)-2(1H)-pyridone

A solution of 90.8 g of 1,2-dihydro-2-oxo-5-(4-pyrimidinyl) nicotinic acid in 900 ml of quinoline is refluxed overnight. The reaction mixture is cooled, poured into 1800 ml of anhydrous ether, stirred for 30 minutes, filtered and the filtered solid washed with 2 l of ether. The solid is dried, recrystallized from 100 ml of hot dimethylformamide and dried to yield 5-(4-pyrimidyl)-2(1H)-pyridone, M.P.>250° C.

Step 5. 3-Bromo-5-(4-pyrimidyl)-2(1H)-pyridone 4.7 g of bromine are added over a period of one minute to a solution of 4.5 g of 5-(4-pyrimidyl)-2(1H)-pyridone in 60 ml glacial acetic acid. The mixture is allowed to cool, stirred at RT for 1 hour and then poured into 100 ml of anhydrous ether and stirred for 30 minutes. The slurry is filtered and the filtered solid washed with ether and dried. The solid is suspended in 100 ml of $H_2O$ and the pH adjusted to about 6 with anhydrous $K_2CO_3$. The mixture is stirred for 15 minutes, filtered, the solid washed with $H_2O$ and briefly dried. The moist solid is added to 40 ml of 5% aqueous hydrochloric acid and the resultant mixture stirred for 30 minutes, diluted with an equal volume of isopropyl alcohol, stirred for an additional 10 minutes and filtered. The resulting solid is washed with isopropyl alcohol ether and dried, giving 3-bromo-5-(4-pyrimidyl)-2(1H)-pyridone as a green powder, M.P.>250° C.

EXAMPLE II

THE PREPARATION OF 3-BROMO-1-METHYL-5-(4-PYRIMIDINYL)-2-PYRIDONE 20 g of 3-bromo-5-(4-pyrimidyl)-2(1H)-pyridone are suspended in 200 ml of dimethylformamide. A solution of 4.6 g of sodium methoxide in 300 ml of dry dimethylformamide and 15 ml of methanol is added to the pyridone suspension with stirring. The reaction mixture is filtered, 5.3 ml of methyl iodide are added to the filtrate and the mixture heated to 60° C. for 2 hours. After cooling to RT, the solution is concentrated in vacuo resulting in a liquid residue which crystallizes out upon addition of distilled $H_2O$. The solid is stirred with 400 ml of distilled $H_2O$, filtered, washed with $H_2O$, isopropyl alcohol, and ether and dried, yielding 3-bromo-1-methyl-5-(4-pyrimidyl)-2-pyridone, M.P. 208°–210° C.

EXAMPLE III

THE PREPARATION OF 3-BROMO-1-ETHYL-5-(4-PYRIMIDINYL)-2-PYRIDONE

A solution of 1.9 g of sodium methoxide in 100 ml of DMF and 30 ml MeOH is added to a suspension of 8.0 g of 3-bromo-5-(4-pyrimidinyl)-2(1H)-pyridone in 100 ml of DMF. Bromoethane (2.7 ml) is added to the mixture, and the mixture is heated to 70° C. for 2 hours. After cooling the mixture to RT, the solvent is evaporated leaving a solid residue which is suspended in 500 ml of distilled $H_2O$, filtered through charcoal and dried. The dried residue is recrystallized from isopropanol with hot filtration to yield 3-bromo-1-ethyl-5-(4-pyrimidinyl)-2-pyridone, M.P. 195°–197° C.

EXAMPLE IV

THE PREPARATION OF 1-BENZYL-3-BROMO-5-(4-PYRIMIDINYL)-2-PYRIDONE

A solution of sodium methoxide (1.85 g) in 100 ml DMF and 30 ml MeOH is added to a stirred, suspension of 3-bromo-5-(4-pyrimidinyl)-2(1H)-pyridone in 100 ml DMF. Benzyl chloride (3.9 ml) is added to the reaction mixture, and the mixture is heated to 70° C. for 2 hours and allowed to cool to RT overnight. The reaction mixture is filtered and the solvent evaporated in vacuo. The residue is suspended in $H_2O$, filtered and dried. The resultant solid is dissolved in hot isopropanol, filtered through charcoal and recrystallized, yielding 1-benzyl-3-bromo-5-(4-pyrimidinyl)-2-pyridone, M.P. 189°–191.5° C.

EXAMPLE V

THE PREPARATION OF 1-BENZYL-3-BROMO-5-(4-PYRIMIDINYL)-2-PYRIDONE METHANESULFONATE

A solution of 1.5 g of methanesulfonic acid in methanol is added to a hot methanol (500 ml) solution containing 4.9 g of 1-benzyl-3-bromo-5-(4-pyrimidinyl)-2-pyridone. The reaction mixture is stirred for 5 minutes at RT and stirred at ice bath temperature until cold. 600 ml of ether are added to the reaction mixture causing the precipitation of a white solid. Stirring at ice bath temperature is continued for 30 minutes. The precipitate is filtered, washed with ether and air dried, yielding the desired methane sulfonate salt, M.P. 217°–218° C.

EXAMPLE VI

THE PREPARATION OF 1-METHYL-5-(4-PYRIMIDINYL)-2-PYRIDONE

A solution of 4.8 g of sodium methoxide in 300 ml of dry DMF and 15 ml of methanol is added to a suspension of 5-(4-pyrimidinyl)-2(1H)-pyridone (2 g) in 200 ml DMF. The reaction mixture is filtered and 5.5 ml of methyl iodide added to the filtrate. The reaction mixture is heated to 60° C. for 2 hours, cooled to RT, and the solvent evaporated in vacuo leaving a liquid residue that crystallizes upon the addition of distilled $H_2O$. The crystalline solid is stirred with 400 ml of distilled $H_2O$, filtered, washed with $H_2O$, isopropyl alcohol, and ether and then air dried to yield the desired 1-methyl-5-(4-pyrimidyl)-2-pyridone, M.P. 147°–149° C.

EXAMPLE VII

THE PREPARATION OF 1-METHYL-5-(4-PYRAZINYL)-2-PYRIDONE

Step 1. α-(2-PYrazinyl)-β-dimethyl aminoacrolein

Dimethylformamide (525 ml) is cooled in an ice bath to 4° C. and 244 g of phosphorous oxychloride are added while stirring over a period of 1 hour 20 minutes and while maintaining a temperature of less than 10° C. Stirring is continued for an additional 30 minutes. 50.0 g of 2-methylpyrazine are added to the reaction mixture over a period of 30 minutes while maintaining the reaction temperature at 8°–11° C. The reaction mixture is allowed to warm to RT followed by heating to 70° C. for a period of 5 hours and allowed to stand at RT overnight. The mixture is cooled in an ice bath and poured into 1500 ml $H_2O$/1.5 kg $K_2CO_3$ over a period of 30 minutes. 80 ml of ethanol in 200 ml of toluene are added to the mixture which is stirred for 1 hour. The precipitated salts are removed by filtration and rinsed with 500 ml ethanol. The aqueous layer is separated and extracted with 500 ml of EtOH/200 ml toluene. The organic extracts are combined and evaporated in vacuo at 45°–50° C. The resultant dark oil residue is evaporated (50°–60° C./0.05 mm) yielding a dark brown solid. The solid is dissolved in hot isopropyl acetate, filtered while hot and the filtrate allowed to cool with stirring. The resultant slurry is cooled with stirring in an ice bath for 45 minutes, filtered and the solid washed with isopropyl acetate. The solid is dissolved in boiling isopropyl acetate and filtered hot. The filtrate is cooled in an ice bath for ½ hour and filtered to yield α-(2-pyrazinyl)-β-dimethylaminoacrolein as a solid, M.P. 103°–104° C.

Step 2. 3-Cyano-5-(4-pyrazinyl)-2(1H)-pyridone 16.3 g of sodium methoxide are added to a solution of 26.6 g of α-(2-pyrazinyl)-β-dimethylamino acrolein and 12.7 g of 2-cyanoacetamide in 400 ml methanol. The mixture is refluxed with stirring for 1 hour, allowed to cool and filtered. The filtered material is washed with methanol and dried yielding a slightly moist, pale green solid which is dissolved in 1250 ml of $H_2O$ and filtered. The aqueous filtrate is adjusted to pH 4–6 with 6N HCl, creating a slurry which is stirred in an ice bath for 30 minutes. The slurry is filtered and the filtered material washed with 200 ml H₂O, 200 ml isopropyl alcohol and 200 ml of ether to yield 3-cyano-5-(4-pyrazinyl)-2(1H)-pyridone as a beige solid, M.P. >250° C.

Step 3. 1,2-Dihydro-2-oxo-5-(2-ovrazinyl)nicotinic acid

A mixture of 25.0 g of 3-cyano-5-(2-pyrazinyl)-2(1H)-pyridone and 500 ml of 50% aqueous sulfuric acid is refluxed for 5 hours and allowed to cool. The mixture is poured onto about 1.5 kg crushed ice with mechanical stirring while cooling in an ice bath. The precipitate is collected, washed with H₂O, ethanol and ether and dried in vacuo overnight at 75° C. The dried solid is added to H₂O and neutralized with NaOH. The neutralized solid is filtered, washed with H₂O, methanol and ether and recrystallized from DMF, yielding the desired nicotinic acid as a white solid, M.P.>250° C.

Step 4. 5-(4-Pyrazinyl)-2(1H)-pyridone 1,2-Dihydro-2-oxo-5-(2-pyrazinyl)nicotinic acid (72.5 g) is added as a fine powder to 800 ml of stirred quinoline heated to just below boiling. The reaction mixture is refluxed for 24 hours, allowed to cool to RT and then placed in an ice bath, and the solid crystallized out. The solid is filtered, washed with ether, dried and recrystallized from isopropanol (first treating with charcoal and filtering while hot) yielding the desired decarboxylated pyridone.

Step 5. 1-Methyl-5-(4-pyrazinyl)-2-pyridone

Sodium hydride (0.75 g) is added to a stirred solution of 5-(2-pyrazinyl)-2(1H) pyridone (2.2 g) in DMF (150 ml). Methyl p-toluene sulfonate (4.0 g) is added to the stirred reaction mixture after 5 minutes of stirring. After 35 minutes reaction time at RT, the reaction mixture is filtered and the filtrate evaporated in vacuum. The oily solid residue is washed with ether, filtered and the dry solid treated with hot acetone. The acetone is filtered and the filtrate evaporated, yielding a solid. The ether filtrate from above is evaporated, yielding a solid which after washing with decane is combined with the acetone filtrate solid. The combined solids are recrystallized from toluene and decane (treated with charcoal and filtered while hot) resulting in the desired 1-methyl pyridone compound, M.P. 165.5°–166.5° C.

EXAMPLE VIII

THE PREPARATION OF 3-BROMO-1-METHYL-5-(2-PYRAZINYL)-2-PYRIDONE 2.5 ml of bromine are added to a solution of 1-methyl-5-(2-pyrazinyl)-2-pyridone (3.5 g) in glacial acetic acid (150 ml). The reaction mixture is filtered and the filtered solid washed with glacial acetic acid. The filtrate is evaporated in vacuum and the oily residue treated with aqueous sodium bisulfate. The filtered solid is suspended in 250 ml of distilled H₂O to which has been added 7 g of sodium bisulfate. A solution of saturated potassium carbonate is added to the suspension to bring the pH back to 6.4. The resulting solid is filtered, washed with H₂O and air dried. The same sodium bisulfate procedure is followed with the oily residue obtained from the evaporated filtrate. The solids are combined, recrystallized from isopropanol with decolorizing charcoal added and filtered off hot. The recrystallized solid is suspended in 50 ml of H₂O containing 10 g of sodium bisulfate and stirred overnight. The suspended solid is filtered and washed with distilled H₂O, recrystallized from isopropanol, filtered, washed with ether and air dried, resulting in the desired 3-bromo-1-methyl-5-(2-pyrazinyl)-2-pyridone, M.P. 196°–197° C.

EXAMPLE IX

THE PREPARATION OF 3-CHLORO-1-METHYL-5-(2-PYRAZINYL)-2-PYRIDONE

About 1.2 ml of condensed chlorine gas is introduced into a reaction mixture comprising 1-methyl-5-(2-pyrazinyl)-2-pyridone (3.2 g) dissolved in 200 ml of glacial acetic acid. After all the chlorine is added, stirring is stopped and the solid product filtered, washed with ether and air dried. The dried solid is suspended in distilled H₂O to which saturated potassium carbonate is added until the pH is greater than 7. The resulting white solid is filtered, recrystallized from isopropanol, and NMR and IR indicate that it is the desired 3-chloro-1-methyl-5-(2-pyrazinyl)-2-pyridone compound, M.P. 197°–198° C.

EXAMPLE X

THE PREPARATION OF 1-ETHYL-5-(2-PYRAZINYL)-2-PYRIDONE

A suspension of 5-(2-pyrazinyl)-2(1H)-pyridone (6.5 g) and 6.6 g of potassium t-butoxide in 250 ml of dry DMF is stirred with warming until all the solid is dissolved. The stirred solution is cooled in an ice bath and 4.6 ml of bromoethane are added when the temperature reaches 5° C. The ice bath is removed and stirring is continued for 45 minutes at which time 0.5 ml of additional bromoethane is added. Stirring is continued over the weekend. 10 g of sodium bisulfate in distilled H₂O are added to the reaction mixture which is filtered. The filtrate is evaporated and the residue taken up in boiling isopropanol. The isopropanol solution is treating with decolorizing charcoal and filtered while hot. The filtrate is evaporated in vacuum to remove residual DMF, resulting in the formulation of a solid. The solid is recrystallized from acetonitrile with hot filtration. The starting material crystallizes out. The acetonitrile mother liquid is evaporated and the residue chromatographed on 100 g of silica gel. The column is eluted with ethyl acetate, toluene and finally with methanol in ethyl acetate. The early fractions are discarded and the latter fractions are combined and recrystallized from hot toluene/decane and air dried, resulting in the desired 1-ethyl-5-(2-pyrazinyl)-2-pyridone, M.P. 119.5°–120.7° C.

EXAMPLE XI

THE PREPARATION OF 3-BROMO-5-(2-PYRAZINYL)-2(1H)-PYRIDONE 3 ml of bromine are added to a stirred suspension of 5-(2-pyrazinyl)-2(1H)-pyridone (9.0 g) in 300 ml of glacial acetic acid warmed to a temperature of 50° C. The mixture is stirred at RT overnight, cooled in an ice bath to 16° C. and filtered. The filtered yellow solid is suspended in 100 ml of distilled H₂O, to which sodium bisulfite is gradually added until the solid appears tan. A saturated potassium carbonate solution is slowly added until the pH is adjusted to 7.4, and the suspension is filtered. The filtered solid is washed with H₂O and dried under high vacuum at 100° C. for 4 hours, giving the desired 3-bromo-5-(2-pyrazinyl)-2(1H)-pyridone which is recrystallized from methanol, M.P.>250° C.

EXAMPLE XII

THE PREPARATION OF 3-BROMO-1-ETHYL-5-(2-PYRAZINYL)-2-PYRIDONE 1.5 g of sodium methoxide is added to a stirred mixture of 3-bromo-5-(2-pyrazinyl)-2(1H)-pyridone (6.3 g) in DMF (200 ml) warmed to a temperature of 80° C. 4 ml of bromoethane are added to the warmed reaction mixture which is stirred for 30 minutes at 80° C. The reaction mixture is cooled to RT, stirred overnight, filtered and the filtrate acidified to pH 5.7 by addition of methanolic HCl. The acidified filtrate is evaporated resulting in a thick red oil. The oil is treated with hot isopropanol and the inorganic salts filtered off. The isopropanol solution is warmed, charcoal added, and filtered while hot. The filtrate is evaporated resulting in a tan solid which is dissolved in warm toluene and chromatographed on a column of silica gel (40 g per g tan solid) dispersed in toluene. The column is eluted increasing concentrations of ethyl acetate in toluene followed by methanol and ethyl acetate. The purified product is recrystallized from decane and toluene. The initial crop of crystals is identified as the O-ethylated product isomer while the addition of toluene caused the crystallization of a second crop of crystals which is identified as the desired N-ethyl pyridone, M.P. 129°–132° C.

EXAMPLE XIII

THE PREPARATION OF 5-(4-PYRIDAZINYL)-2-(1H) PYRIDONE

A suspension of 2-oxo-5-(4-pyridazinyl)(1H) nicotinic acid (78.4 g) in 670 ml of hot quinoline is heated to reflux under $N_2$ overnight. The reaction mixture is cooled in an ice both, causing a solid to crystallize. The solid is filtered, washed with ether and air dried. The dried solid is washed with a boiling mixture of isopropanol/methanol/DMF, cooled in an ice bath, filtered, washed with ether and air dried, resulting in the desired 5-(4-pyridazinyl)-2-(1H)-pyridone as a crystalline solid, M.P.>250° C.

EXAMPLE XIV

THE PREPARATION OF 3-BROMO-5-(4-PYRIDAZINYL)-2(1H) PYRIDONE 5.0 g of 5-(4-pyridazinyl)-2(1H) pyridone are suspended in 150 ml of glacial acetic acid. After warming the suspension to 50° C., heating is discontinued and 2.2 ml of bromine are added dropwise to the stirred suspension and the reaction mixture stirred overnight. The resulting precipitate is filtered, washed with ether, air dried, dissolved in distilled water treated with aqueous sodium bisulfite, and the pH adjusted to 6.4 by adding a solution of 50% NaOH. An equivalent volume of isopropanol is added to the mixture which is then evaporated. The solid residue is treated with boiling methanol and filtered while hot. The methanol filtrate is evaporated and the solid residue treated with boiling isopropanol. The resulting solid is recrystallized from acetonitrile and isopropanol and dried under high vacuum to give the desired 3-bromo pyridone product, M.P.>250° C. (HCl).

EXAMPLE XV

THE PREPARATION OF 1-METHYL-5-(4-PYRIDAZINYL)-2-PYRIDONE 4.02 g of NaH-oil dispersion is suspended in petroleum ether under $N_2$ and the ether removed. DMF (75 ml) is added as a suspendant and a solution of 15.0 g of 5-(4-pyridazinyl)-2(1H)-pyridone in DMF (300 ml) added to the suspension which is stirred and cooled in an ice bath to 10° C. A solution of methyl p-toluene sulfonate (17.7 g) in DMF (25 g) is added to the reaction mixture and stirring is continued for 40 minutes. The reaction mixture is evaporated, resulting in a wet solid residue. This solid is air dried, then suspended in ether (900 ml), filtered, air dried, dissolved in distilled $H_2O$, acidified with 6N HCl and extracted with ether. The aqueous phase is readjusted to pH 10.0 and extracted with methylene chloride. The organic extracts are filtered through cotton, combined, dried over anhydrous sodium sulfate and evaporated to a solid residue. The aqueous phase is diluted with an equivalent volume of isopropanol and slowly evaporated. The solid residue from the aqueous phase is treated with 1500 ml of boiling isopropanol, hot filtered and the filtrate evaporated. The aqueous phase solid residue is again heated with boiling isopropanol (800 ml), filtered hot and evaporated. The residues from both aqueous and organic phases are dissolved in boiling chloroform, treated with charcoal and hot filtered. The chloroform solution is cooled in an ice bath and 1½ equivalent volumes of ether are added resulting in a solid precipitate. The solid is filtered, washed with ether and air dried, yielding the desired product, 1-methyl-5-(4-pyridazinyl)-2-pyridone which is recrystallized from boiling 1-butanol and ether. After air drying, the drying is continued under high vacuum at 88° for 7 hours, resulting in the dry solid, 1-methyl-5-(4-pyridazinyl)-2-pyridone, M.P.>250° C.

The following list of compounds may be prepared according to the above-described reaction sequences and using analogous reaction conditions and starting materials, which are either commercially available or prepared by methods known to those skilled in the art.

TABLE A 6-methyl-5-(2-pyrimidinyl)-2(1H)-pyridone
6-methyl-5-(4-pyrimidinyl)-2(1H)-pyridone
6-ethyl-5-(3-pyridazinyl)-2(1H)-pyridone
6-ethyl-5-(4-pyridazinyl)-2(1H)-pyridone
6-ethyl-5-(2-pyrazinyl)-2(1H)-pyridone
3-bromo-6-methyl-5-(2-pyrimidinyl)-2(1H)-pyridone
3-bromo-6-methyl-5-(4-pyrimidinyl)-2(1H)-pyridone
3-chloro-6-ethyl-5-(3-pyridazinyl)-2(1H)-pyridone
3-bromo-6-ethyl-5-(4-pyridazinyl)-2(1H)-pyridone
3-chloro-6-ethyl-5-(2-pyrazinyl)-2(1H)-pyridone
6-methyl-3-trifluoromethyl-5-(2-pyrimidinyl)-2(1H)-pyridone
6-methyl-3-trifluoromethyl-5-(4-pyrimidinyl)-2(1H)-pyridone
6-ethyl-3-trifluoromethyl-5-(3-pyridazinyl)-2(1H)-pyridone
6-ethyl-3-trifluoromethyl-5-(4-pyridazinyl)-2(1H)-pyridone
6-ethyl-3-trifluoromethyl-5-(2-pyrazinyl)-2(1H)-pyridone
1,6-dimethyl-5-(2-pyrimidinyl)-2-pyridone
1-ethyl-6-methyl-5-(4-pyrimidinyl)-2-pyridone
1,6-diethyl-5-(3-pyridazinyl)-2-pyridone 6-ethyl-1-methyl-5-(4-pyridazinyl)-2-pyridone
1,6-diethyl-5-(2-pyrazinyl)-2-pyridone
3-bromo-1,6-dimethyl-5-(2-pyrimidinyl)-2-pyridone
3-bromo-1-ethyl-6-methyl-5-(4-pyrimidinyl)-2-pyridone
3-chloro-1,6-diethyl-5-(3-pyridazinyl)-2-pyridone
3-bromo-6-ethyl-1-methyl-5-(4-pyridazinyl)-2-pyridone
3-chloro-1,6-diethyl-5-(2-pyrazinyl)-2-pyridone
1,6-dimethyl-3-trifluoromethyl-5-(2-pyrimidinyl)-2-pyridone
1-ethyl-6-methyl-3-trifluoromethyl-5-(4-pyrimidinyl)-2-pyridone
1,6-diethyl-3-trifluoromethyl-5-(3-pyridazinyl)-2-pyridone
6-ethyl-1-methyl-3-trifluoromethyl-5-(4-pyridazinyl)-2-pyridone
1,6-diethyl-3-trifluoromethyl-5-(2-pyrazinyl)-2-pyridone
4,6-dimethyl-5-(2-pyrimidinyl)-2(1H)-pyridone
4-ethyl-6-methyl-5-(4-pyrimidinyl)-2(1H)-pyridone
4,6-diethyl-5-(3-pyridazinyl)-2(1H)-pyridone
6-ethyl-4-methyl-5-(4-pyridazinyl)-2(1H)-pyridone
4,6-diethyl-5-(2-pyrazinyl)-2(1H)-pyridone
3-bromo-4,6-dimethyl-5-(2-pyrimidinyl)-2(1H)-pyridone
3-bromo-4-ethyl-6-methyl-5-(4-pyrimidinyl)-2(1H)-pyridone
3-chloro-4,6-diethyl-5-(3-pyridazinyl)-2(1H)-pyridone
3-bromo-6-ethyl-4-methyl-5-(4-pyridazinyl)-2(1H)-pyridone
3-chloro-4,6-diethyl-5-(2-pyrazinyl)-2(1H)-pyridone
4,6-dimethyl-3-trifluoromethyl-5-(2-pyrimidinyl)-2(1H)-pyridone
4-ethyl-6-methyl-3-trifluoromethyl-5-(4-pyrimidinyl)-2(1H)-pyridone
4,6-diethyl-3-trifluoromethyl-5-(3-pyridazinyl)-2(1H)-pyridone
6-ethyl-4-methyl-3-trifluoromethyl-5-(4-pyridazinyl)-2(1H)-pyridone
4,6-diethyl-3-trifluoromethyl-5-(2-pyrazinyl)-2(1H)-pyridone
1,4,6-trimethyl-5-(2-pyrimidinyl)-2-pyridone
1,4-diethyl-6-methyl-5-(4-pyrimidinyl)-2-pyridone
1,4,6-triethyl-5-(3-pyridazinyl)-2-pyridone
1,4-dimethyl-6-ethyl-5-(4-pyridazinyl)-2-pyridone
1,4,6-triethyl-5-(2-pyrazinyl)-2-pyridone
3-bromo-1,4,6-trimethyl-5-(2-pyrimidinyl)-2-pyridone
3-bromo-1,4-diethyl-6-methyl-5-(4-pyrimidinyl)-2-pyridone
3-chloro-1,4,6-triethyl-5-(3-pyridazinyl)-2-pyridone
3-bromo-1,4-dimethyl-6-ethyl-5-(4-pyridazinyl)-2-pyridone
3-chloro-1,4,6-triethyl-5-(2-pyrazinyl)-2-pyridone
3-trifluoromethyl-1,4,6-trimethyl-5-(2-pyrimidinyl)-2-pyridone
1,4-diethyl-6-methyl-3-trifluoromethyl-5-(4-pyrimidinyl)-2-pyridone
1,4,6-triethyl-3-trifluoromethyl-5-(3-pyridazinyl)-2-pyridone
1,4-diethyl-6-ethyl-3-trifluoromethyl-5-(4-pyridazinyl)-2-pyridone
1,4,6-triethyl-3-trifluoromethyl-5-(2-pyrazinyl)-2-pyridone The compounds of Formula I possess positive inotropic activity and are useful as cardiotonic agents in the treatment of humans and other mammal for cardiac disorders including congestive heart failure. One of the advantages of the present development is that use of compounds within the scope of Formula I in accordance with the treatment aspects of the present invention results in minimal or no undesirable side effects, for example, gastrointestinal irritation or stomach ulceration. Such effects have been observed during the administration of heretofore used 5-pyridyl-pyridone cardiotonics, including 3-amino-5-(4-pyridyl)-2(1H)-pyridone (known as "amrinone").

The effectiveness of the compounds of this invention as inotropic agents may be determined by the following pharmacologic tests which evaluate the change in cardiac contractile force upon exposure to a dose of said compounds. The anesthetized dog procedure is a standard test procedure; the inotropic results of this procedure generally correlate with the inotropic activity found in human patients.

Anesthetized Dog Procedure

Male mongrel dogs are anesthetized with pentobarbital (35 mg/kg i.v.) and intubated. Femoral artery and veins are cannulated for measurement of blood pressure and injection of compounds, respectively. A catheter connected to a Statham transducer is inserted into the left ventricle via the right carotid artery for measurement of left ventricular pressure, left ventricular end diastatic pressure and dP/dt. Lead II ECG and heart rate are also monitored. All parameters are measured on a Beckman Dynagraph.

The results of the anesthetized dog test show that the compounds of this invention exhibit positive inotropic activity and show dose related increases in contractile force with relatively small increases in heart rate.

A second test procedure which has been found to be an efficient means for ascertaining the inotropic activity of the compounds of this invention is described below.

Guinea Pig Atria Inotropic Screening at Low Calcium Concentrations

Guinea pigs are stunned by a sudden blow to the head; their chests are opened and hearts excised and placed in Kreb's medium (concentrations, mM: NaCl, 118.39; KCl, 4.70; $MgSO_4$, 1.18; $KH_2PO_4$, 1.18; $NaHCO_3$, 25.00; glucose, 11.66; and $CaCl_2$, 1.25) gassed with a mixture of 95% $O_2$–5% $CO_2$. Left atria are removed and inserted into warmed (33° C.) double jacketed tissue chambers containing oxygenated Kreb's medium (as above). The upper end of each tissue is attached to a Statham Universal Transducing Cell via a Statham Microscale Accessory. Resting tension on each tissue is set at 1 g and adjusted periodically.

Massive field stimulation is acheived via a pair of platinum or silver electrodes placed on opposite sides of the tissue. Electrodes are made from 20-gauge silver wire wound into a tight coil approximately 12–14 mm in diameter. Electrodes are connected to a Grass stimulator via a Grass constant current unit. Tissues are driven at 90 pulses per minute with a 5 msec duration at current levels 20% greater than threshold for continuous beat.

Cumulative concentrations of test drugs are added to the tissue bath at intervals sufficient to allow developed tension to peak at a new level.

The increase in developed tension in each tissue for each compound concentration is measured, and the results are averaged and used to construct cumulative concentration-response curves. Slopes for these regressions are calculated via the method of Finney (1971) and compared using Student's t-test.

The compounds of this invention can be normally administered orally or parenterally, in the treatment of cardiac disorders such as heart failure in humans or other mammals.

The compounds of this invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of inotropic active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, suitably buffered, made isotonic with sufficient saline or glucose and sterilized by heating or by microfiltration.

The dosage regimen in carrying out the methods of this invention is that which insures maximum therapeutic response until improvement is obtained and thereafter the minimum effective level which gives relief. Thus, in general, the dosages are those that are therapeutically effective in increasing the contractile force of the heart or in the treatment of cardiac failure. In general, the oral dose may be between about 0.01 mg/kg and about 50 mg/kg (preferably in the range of 0.1 to 10 mg/kg), and the i.v. dose about 0.005 to about 30 mg/kg (preferably in the range of 0.01 to 3 mg/kg), bearing in mind, of course, that in selecting the appropriate dosage in any specific case, consideration must be given to the patient's weight, general health, age, and other factors which may influence response to the drug. The drug may be administered orally 1 to 4 times per day, preferably twice daily.

I claim:

1. 1-Ethyl-5-(4-pyrimidinyl)-2-pyridone or a pharmaceutically acceptable salt thereof.

* * * * *